United States Patent [19]

Klunder et al.

[11] Patent Number: 5,702,410
[45] Date of Patent: Dec. 30, 1997

[54] BALLOON CATHETER WITH BALLOON PROTECTION SHEATH

[75] Inventors: Rento Willem Klunder, Groningen; Gerda Hendrika Maria Van Werven-Franssen, Roden, both of Netherlands

[73] Assignee: Cordis Corporation, Miami Lakes, Fla.

[21] Appl. No.: 651,926

[22] Filed: May 21, 1996

[30] Foreign Application Priority Data

May 22, 1995 [NL] Netherlands .............................. 1000413

[51] Int. Cl.⁶ .................................................. A61M 29/00
[52] U.S. Cl. .................................................. 606/194; 606/96
[58] Field of Search ........................ 606/1, 108, 191–195; 604/96–101, 280

[56] References Cited

U.S. PATENT DOCUMENTS

| | | |
|---|---|---|
| 4,338,942 | 7/1982 | Fogarty .................................. 606/194 |
| 4,493,711 | 1/1985 | Chin et al. . |
| 5,015,231 | 5/1991 | Keith et al. ............................ 604/96 |
| 5,116,318 | 5/1992 | Hillstead . |
| 5,211,654 | 5/1993 | Kaltenbach . |
| 5,246,421 | 9/1993 | Saab . |
| 5,342,305 | 8/1994 | Shonk ..................................... 604/101 |
| 5,352,236 | 10/1994 | Jung et al. . |
| 5,366,472 | 11/1994 | Hillstead . |
| 5,424,709 | 6/1995 | Gambale . |
| 5,425,710 | 6/1995 | Khair et al. . |
| 5,501,667 | 3/1996 | Verduin, Jr. ........................... 604/96 |
| 5,593,412 | 1/1997 | Martinez et al. ...................... 606/108 |

FOREIGN PATENT DOCUMENTS

| | | |
|---|---|---|
| 366904 | 5/1982 | Austria . |
| 0331040 | 9/1989 | European Pat. Off. . |

Primary Examiner—William Lewis
Attorney, Agent, or Firm—Henry W. Collins

[57] ABSTRACT

The balloon catheter comprises a basic tubular body having a distal end and a proximal end. A balloon member is arranged on the distal end and, close to the balloon member, is arranged an elongate, elastic balloon protection sheath. A pull thread is connected to an end of the sheath facing toward the balloon member and extends to the proximal end of the basic tubular body. The sheath can be pulled over the balloon member by pulling the pull thread.

7 Claims, 2 Drawing Sheets

BALLOON CATHETER WITH BALLOON PROTECTION SHEATH

BACKGROUND OF THE INVENTION

1. Field of the Invention

The present invention relates to a balloon catheter comprising a basic tubular body having a distal end and a proximal end. A balloon member is arranged on the distal end and close to the balloon member is arranged an elongate, elastic balloon protection sheath which can be pulled over the balloon.

2. Description of the Related Art Including Information Disclosed under 37 CFR §§1.97–1.99

Balloon catheters, of the type with which the present invention is concerned, are well known in the field of angioplasty. Such balloon catheters are used, for example, to dilate a stenosis in the blood circulation of a patient. The balloon member must, on the one hand, be sufficiently strong to be able to safely withstand the loads occurring during insertion and treatment. On the other hand, it is desired that at the position of the balloon member, which normally determines the largest diameter of the catheter, the catheter be embodied with the smallest possible diameter to enable insertion of the balloon catheter into the patient through the smallest possible introducer.

Examples of prior art balloon catheters utilizing a sheath or outer wall protection for the balloon are disclosed in the following U.S. Patents and foreign patent publications:

| U.S. Pat. No. | Patentee |
| --- | --- |
| 4,493,711 | Chin et al. |
| 5,116,318 | Hillstead |
| 5,211,654 | Kaltenbach |
| 5,246,421 | Saab |
| 5,352,236 | Jung et al. |
| 5,424,709 | Gambale |
| 5,425,710 | Khair et al. |
| European Patent No. | Inventor |
| 0 331 040 | Planck |
| Austrian Patent No. | Patentee |
| 366904 | Pristauz |

SUMMARY OF THE INVENTION

According to the present invention, there is provided a balloon catheter comprising a basic tubular body having a distal end and a proximal end. A balloon member is arranged on the distal end and, close to the balloon member, is arranged an elongate, elastic balloon protection sheath. A pull thread is connected to an end of the sheath facing toward the balloon member and extends to the proximal end of the basic tubular body. The sheath can be pulled over the balloon member by pulling the pull thread.

In the situation where the sheath over the balloon member uses at least one pull thread, the balloon protection sheath provides a great resistance to damage to the balloon member while, at the same time, not enlarging the effective diameter of the balloon catheter at the position of the balloon member when the balloon catheter is inserted, because it is located off to the side of the balloon member on or within an adjoining portion of the basic tubular body.

After insertion of the balloon catheter in the situation where the balloon protection sheath is pushed off the balloon member and, thus, has the smallest possible diameter, the balloon protection sheath can be slid onto the balloon member by pulling on the pull thread, whereafter the balloon member can be expanded in the usual manner. In the expanded active situation, the balloon member is optimally protected against mechanical influences from outside by the balloon protection sheath.

The balloon protection sheath can be a sleeve slidable over the basic body of the catheter and is elastically stretchable in the longitudinal direction of the basic tubular body and has an end remote from the balloon member fixedly connected to the basic tubular body. The position of the balloon protection sheath then is determined clearly so that reliable operation can be achieved.

Preferably, the basic tubular body has at least one lumen and the pull thread is guided through the lumen. By guiding the pull thread through the lumen, the pull thread and the basic tubular body act, respectively, as the inner cable and the outer cable of a pull cable. A pulling force exerted on the pull thread does not then influence the location of the balloon catheter, nor is there a danger of the pull thread, for instance in a bend, being pressed with force against the wall of the blood vessel, whereby there would be a risk of trauma.

Also, preferably, the balloon protection sheath is arranged close to a relatively proximal end of the balloon member and the pull thread first extends from the balloon protection sheath in a distal direction, is then guided through an orifice at the distal end of the basic tubular body to the lumen and then extends through the lumen to the proximal end of the basic tubular body. This ensures that the balloon protection sheath does not slide over the balloon member during insertion of the balloon catheter. The relative movement of the balloon catheter along the wall of the blood vessel shifts the sheath in the direction toward the proximal end of the basic tubular body, whereby the sheath is held in place clear of the balloon member.

In one preferred embodiment, two pull threads are provided, each connected to one end to the elongate balloon protection sheath. In this way, the protection sheath can be pulled over, as well as pulled off, the balloon.

Also in one preferred embodiment, the balloon protection sheath is made from a woven material, like a nylon stocking, so that it can be stretched elastically and, after removal of a force causing the stretching, returns to its original shape, i.e. clear of the balloon member.

DESCRIPTION OF THE PREFERRED EMBODIMENT(S)

Figure 1:
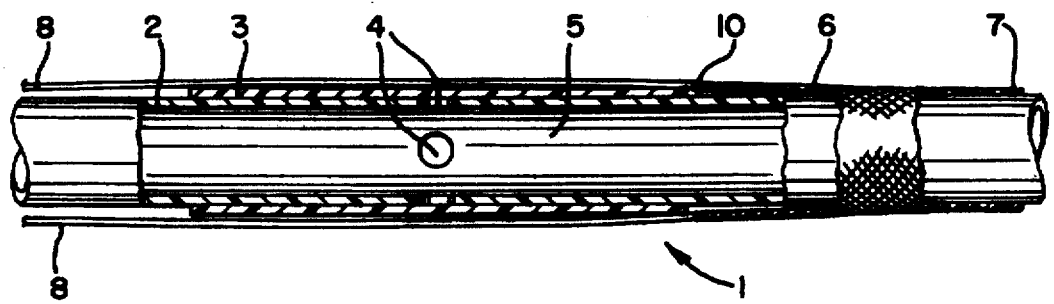
FIG. 1 is a longitudinal view with portions broken away of a balloon catheter constructed according to the teachings of the present invention and shows the position of a balloon member at a first location relative to a balloon protection sheath.
Figure 2:
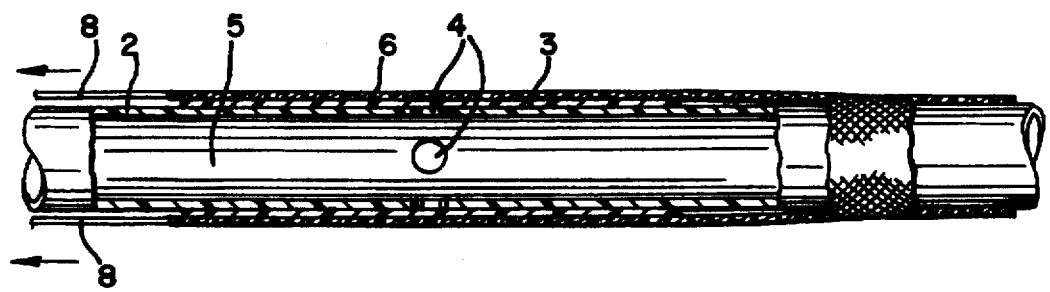
FIG. 2 is a longitudinal view, similar to the view shown in FIG. 1, with portions broken away, of the balloon catheter, but shows the balloon protection sheath pulled over the balloon member.

Referring now to the drawings in greater detail, a balloon catheter 1 is shown in FIGS. 1 and 2 and comprises a basic tubular body 2, a distal end part of which is shown. Arranged around the distal end part is a balloon member 3 which is fixedly and sealingly connected at either end to the outer surface of the basic tubular body 2.

Extending in the basic tubular body 2, in this embodiment, is one lumen 5 which connects at the proximal end (not shown) to a connecting member through which a fluid under pressure can be supplied. This fluid travels via the apertures 4 in the wall of the basic tubular body 2 into the interior of the balloon member 3 which can thereby be expanded.

Close to the balloon member 3, an elastic balloon protection sheath 6 is arranged around the basic tubular body 2, which sheath can be pulled over the balloon member 3 with two pull threads 8 which are fastened to the end of the sheath 6 facing toward the balloon member 3 and which extend from this end 10 to the proximal end of the basic tubular body 2.

The balloon protection sheath 6 is fixedly connected with its opposite end, that is, the end 7 remote from balloon member 3, to the basic tubular body 2. The balloon protection sheath 6 is made of elastic material and, for instance, of material woven in the manner of nylon stockings, so that in the released state, the sheath 6 is contracted onto the relatively distal end of balloon member 3.

In this situation shown in FIG. 1, the balloon catheter 1 has a relatively limited diameter which is effectively no larger than the diameter of the basic tubular body 2 at the position of the balloon member 3. The sheath 6 does not lie on the balloon member 3, thus causing no enlargement of the diameter. The balloon catheter 1 can thus be introduced into a patient by means of an introducer of relatively limited diameter.

As soon as the balloon member 3 is arranged at the intended location, for instance at the position of a stenosis, the sheath 6 is pulled over the balloon member 3 by the treating physician pulling on the end part of the pull threads 8 situated at the proximal end of the balloon catheter 1. Fluid is subsequently fed under pressure via lumen 5 and apertures 4 therein into the interior of the balloon member 3 which thereby expands in the manner shown in FIG. 3. The protection sheath 6 situated around the balloon member 3 also expands because it is elastic but at the same time continues to form a protective layer around the balloon member 3, so that the actual balloon member 3 is protected against damage. In the case of, for instance, a calcified stenosis, the protection sheath 6 prevents damage to the balloon member 3.

Instead of being used for an angioplasty procedure, the balloon catheter 1, according to the invention, also can be used to arrange a stent or graft. Due to the good protection provided to the balloon member 3 by the protection sheath 6, the chance of damage to the balloon member 3 is also minimal in these applications.

At the end of the treatment, the balloon member 3 is again allowed to contract by removing the pressure on the supplied fluid. The sheath 6 likewise contracts due to its elasticity. By releasing the pull threads 8, the sheath 6 can slide back again into its original position, as shown in FIG. 1. In this situation, the balloon catheter 1 can be taken out.

Figure 3:
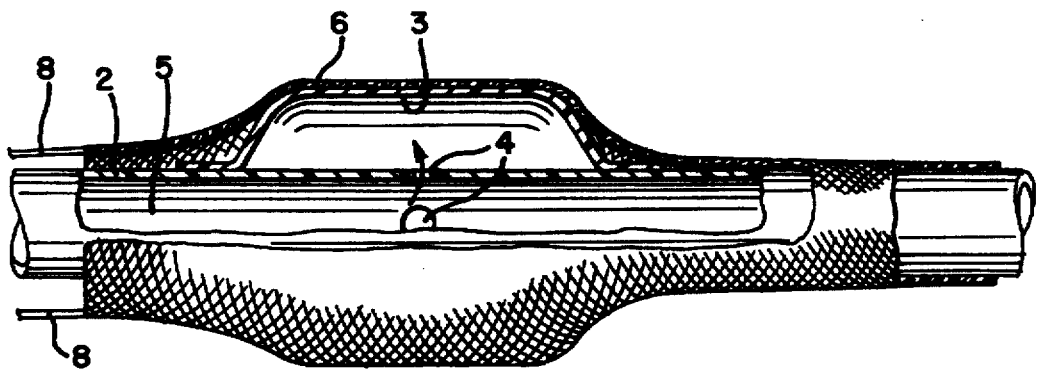
FIG. 3 is a longitudinal view, similar to the view shown in FIG. 2, with portions broken away, of the balloon catheter shown in FIG. 2, but shows the balloon member in an inflated state.
Figure 4:
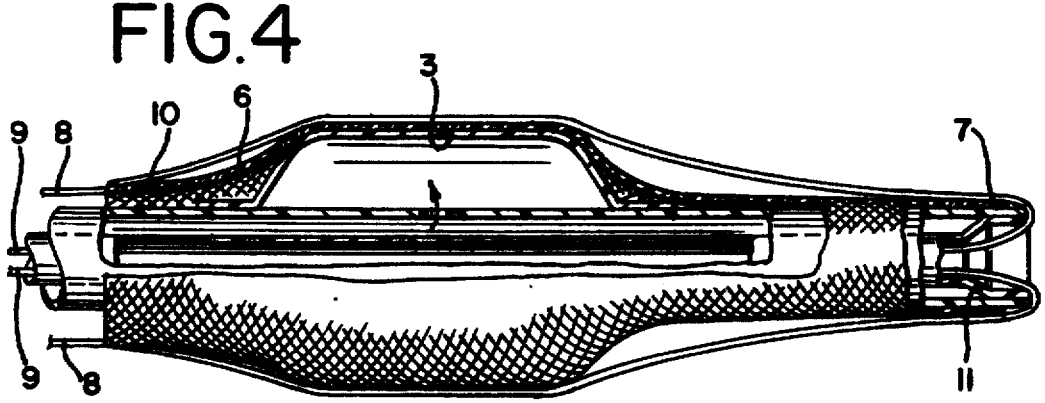
FIG. 4 is a longitudinal view, similar to the view shown in FIG. 3, with portions broken away, of another embodiment of the balloon catheter constructed according to the teachings of the present invention.

In the embodiment shown in FIGS. 1–3, the protection sheath 6 is, as stated, of elastically stretchable material. The sheath, however, also can be manufactured from material which is not elastically stretchable in the longitudinal direction. In that case, the sheath can be moved back again to its starting position by an additional set of pull threads acting in the opposing direction. Such an embodiment is shown in FIG. 4. The pull threads 9 are herein fixed at substantially the same place on the sheath 6 as the pull threads 8. Pull threads 9 extend first in the direction of the distal end of the balloon catheter 1, shown on the right of FIG. 4, and are then guided inside an inner tubular member 11 received in the basic tubular body 2. Pull threads 9 run through a lumen of this inner tubular member 11 to the proximal end where they can be controlled by the treating physician. Although, in this embodiment, the right-hand end of the protection sheath 6 is fixedly connected to the basic tubular body, it is, of course, also possible to connect the left-hand end fixedly to the basic tubular body 2. Pull threads 9 then serve to pull the sheath 6 over the balloon member 3 and the threads 8 to retract it.

Figure 5:
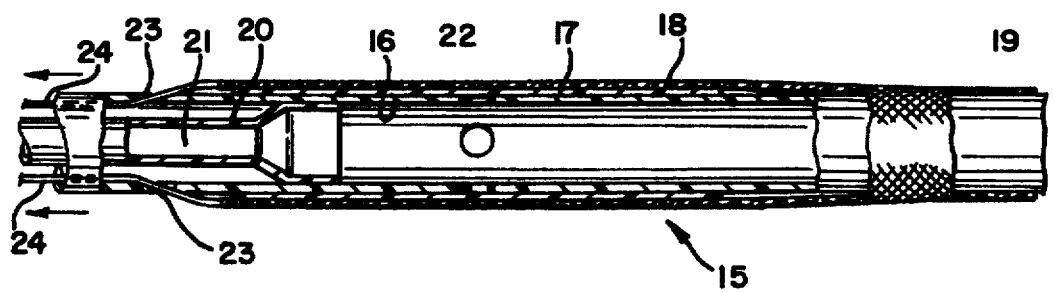
FIG. 5 is a longitudinal view, with portions broken away, of still another embodiment of a balloon catheter constructed according to the teachings of the present invention.

In the balloon catheter 15 shown in FIG. 5, a balloon member 17 is arranged around the distal end of a basic tubular body 16. In a manner corresponding with the foregoing embodiment, a protection sheath 18 is arranged with its relatively distal end 19 connected to the basic tubular body 16. Connected to the relatively proximal end of the protection sheath 18 are pull threads 24 which are guided through orifices 23 in the basic tubular body 16. The pull threads 24 extend through the lumen of basic tubular body 16 to the proximal end where they can be operated.

Received in the lumen of the basic tubular body 16 is an inner tubular member 20, via the lumen 21 of which fluid under pressure can be supplied which can flow via apertures 22 into the interior of the balloon member 17 in order to expand it. It will be apparent that the lumen of the basic tubular body 16 is closed at the distal end in order to enclose the fluid under pressure.

Figure 6:
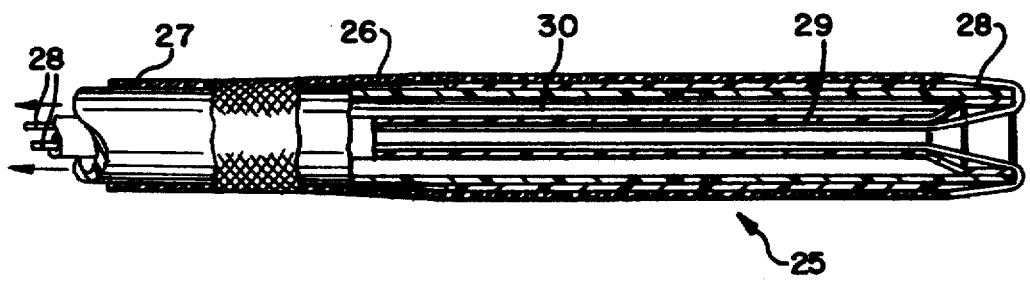
FIG. 6 is a longitudinal view, with portions broken away, of yet another embodiment of a balloon catheter constructed according to the teachings of the present invention.
Figure 7:
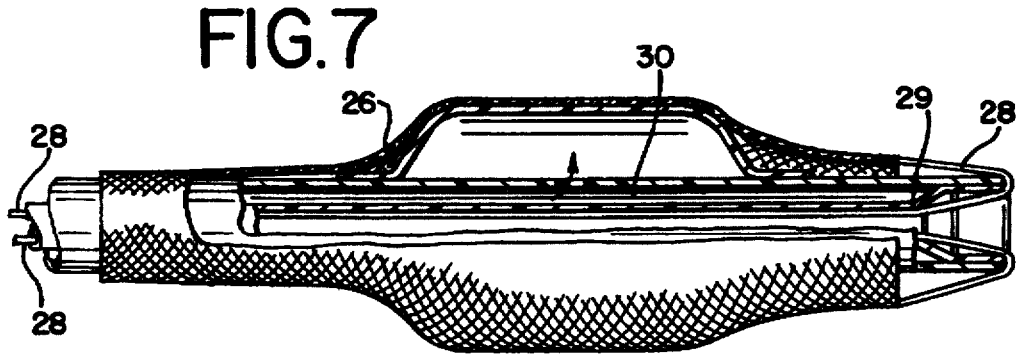
FIG. 7 is a longitudinal view, with portions broken away, of the balloon catheter shown in FIG. 6, but shows a balloon member of the balloon catheter in an inflated state.

In the embodiment of the balloon catheter 25 shown in FIGS. 6 and 7, a protection sheath 26 is arranged on the relatively proximal side of a balloon member. The end 27 of the protection sheath 26 remote from the balloon member, that is, the relatively proximal end therein, is again fixedly connected to the basic tubular body and the sheath 26 can be pulled over the balloon member using pull threads 28 which are fastened to the relatively distal end of the protection sheath 26 and which run first in a distal direction and at the end of the balloon catheter 25 are diverted into the lumen of the balloon catheter 25 in order to extend through this lumen from the distal end to the proximal end. The attendant physician can operate the pull threads 28 at the proximal end to pull the protection sheath 26 over the balloon member.

The pull threads 28 are more particularly received in the lumen of an inner tubular member 29 which is sealingly connected with its distal end part to the wall of the lumen of the basic tubular body. A fluid under pressure for expanding the balloon member can be supplied via the annular channel 30 remaining between the wall of the lumen of the basic tubular body and the inner tubular member.

FIG. 7 shows the catheter of FIG. 6 with the balloon in an expanded state. Via the annular channel 30, fluid under pressure is fed into the interior of the balloon member in order to expand it.

According to another embodiment (not shown), the balloon protection sheath can be accommodated in the position of non-use in the catheter basic tubular body. This can be in a lumen or a cavity specially formed for this purpose. When the sheath is placed in the position of use, it is then pulled outward and over the balloon with the pull thread or threads.

From the foregoing description, it will be apparent that the balloon catheter with balloon protection sheath of the present invention has a number of advantages, some of which have been described above and others of which are inherent in the invention. Also it will be understood that modifications can be made to the balloon catheter with balloon protection sheath described above without departing from the teachings of the present invention. Accordingly, the scope of the invention is only to be limited as necessitated by the accompanying claims.

We claim:

1. A catheter comprising a basic tubular body having a distal end and a proximal end, a balloon member which is arranged on the distal end, an elongate, elastic balloon protection sheath which is arranged on or in the basic tubular body close to the balloon member and at least one pull thread connected to the end of the sheath facing toward the balloon member, the at least one pull thread extending to the proximal end of the basic tubular body for being pulled to pull the sheath over the balloon member.

2. The catheter as claimed in claim 1 wherein the balloon protection sheath is elastically stretchable in a longitudinal direction and is fixedly connected to the basic tubular body with the end of the sheath which is remote from the balloon member.

3. The catheter as claimed in claim 1 wherein the basic tubular body has at least one lumen therein and the pull thread is guided through the lumen.

4. The catheter as claimed in claim 3, wherein the balloon protection sheath is arranged close to the relatively proximal end of the balloon member and the pull thread first extends from the balloon protection sheath in distal direction, is then guided to the lumen through an orifice at the distal end of the basic tubular body and subsequently extends through the lumen to the proximal end of the basic tubular body.

5. The catheter as claimed in claim 1 comprising at least two pull threads, each connected to one end of the sheath and acting in opposing directions.

6. The catheter as claimed in claim 1 wherein the balloon protection sheath is made of woven material.

7. The catheter as claimed in claim 1 wherein the balloon catheter has a sheath receiving space in the basic tubular body for receiving the sheath when it is not being used and pull thread means are provided for moving the sheath out of and into the space.

* * * * *